United States Patent [19]

Burgoyne, Jr. et al.

[11] Patent Number: 5,068,435
[45] Date of Patent: Nov. 26, 1991

[54] ORTHO-ALKYLATED AROMATIC AMINES VIA GAMMA ALUMINA CATALYST

[75] Inventors: William F. Burgoyne, Jr., Emmaus, Pa.; Dale D. Dixon, Venice, Fla.

[73] Assignee: Air Products and Chemicals, Inc., Allentown, Pa.

[21] Appl. No.: 173,221

[22] Filed: Mar. 25, 1988

Related U.S. Application Data

[63] Continuation-in-part of Ser. No. 796,465, Nov. 8, 1985, Pat. No. 4,740,620.

[51] Int. Cl.$^5$ ............................................ C07C 201/68
[52] U.S. Cl. .................................. 564/409; 564/307; 564/308; 564/309; 564/330; 564/335; 564/437
[58] Field of Search ............... 564/330, 409, 437, 308, 564/307, 309, 335

[56] References Cited

U.S. PATENT DOCUMENTS

| | | | |
|---|---|---|---|
| 2,194,079 | 3/1940 | Smith et al. | 564/409 |
| 2,762,845 | 9/1956 | Stroh et al. | 260/578 |
| 3,275,690 | 9/1966 | Stroh et al. | 260/576 |
| 3,649,693 | 3/1972 | Napolitano | 260/578 |
| 3,670,030 | 6/1972 | Sparks | 564/409 X |
| 3,923,892 | 12/1975 | Klopfer | 260/578 |
| 4,351,958 | 9/1982 | Takahara et al. | 564/437 X |
| 4,400,537 | 8/1983 | Weil | 564/437 X |
| 4,565,834 | 1/1986 | Buysch et al. | 564/434 X |
| 4,740,620 | 4/1988 | Dixon et al. | 564/307 X |
| 4,792,633 | 12/1988 | Wojtkowski | 568/50 X |

FOREIGN PATENT DOCUMENTS

| | | |
|---|---|---|
| 1051271 | 7/1955 | Fed. Rep. of Germany . |
| 1406739 | 7/1964 | France . |
| 56-110652 | 2/1980 | Japan . |
| 6407636 | 7/1964 | Netherlands . |
| 414574 | 12/1933 | United Kingdom . |
| 414574 | 8/1934 | United Kingdom ................ 564/409 |
| 846226 | 12/1958 | United Kingdom . |

OTHER PUBLICATIONS

Zollner, Gy and J. Marton, "Some Aspects of Ethylation of Aniline in the Vapour Phase", 5/12/56, pp. 321-329.

Primary Examiner—Richard L. Raymond
Attorney, Agent, or Firm—Russell L. Brewer; James C. Simmons; William F. Marsh

[57] ABSTRACT

This invention relates to a process for producing ring alkylated aromatic amines. In the process an aromatic amine is reacted with an olefin using gamma alumina as a catalyst. Under the conditions of the process the catalyst is extremely active and with amines that are capable of alkylation at the ortho and para positions, high selectivity to the ortho alkylated isomer can be achieved.

The catalyst is also effective for producing unsymmetrical disubstituted alkyl aromatic amines, e.g., ethyl or propyl toluidine where one ortho position is substituted with a methyl group and the other substituted with an ethyl or propyl group.

9 Claims, No Drawings

ORTHO-ALKYLATED AROMATIC AMINES VIA GAMMA ALUMINA CATALYST

CROSS-REFERENCE TO RELATED APPLICATION

This invention is a continuation-in-part of U.S. Ser. No. 06,796,465, now U.S. Pat. No. 4,740,620 having a filing date of Nov. 8, 1985, the subject matter being incorporated by reference and commonly assigned.

BACKGROUND OF THE INVENTION

Processes for alkylating a variety of alkylatable aromatic compounds by contacting such compounds with hydrocarbon radical providing source such as an olefin or alcohol are widely known. Typically, alkylatable aromatic compounds are mononuclear aromatic compounds themselves or those substituted with a hydroxyl, amine or an ether group. The alkylation has been carried out in the presence of homogeneous and heterogeneous catalyst systems.

Ring alkylated aromatic amines have been some of the products produced by alkylation procedures. Ring alkylated aromatic amines have a variety of uses in chemical synthesis. Some of the early uses were intermediates for substituted isocyanates, herbicidal compositions, dyestuffs and textile auxiliary agents. More recently aromatic amines have been utilized as chain lengthening or cross-linking components in polyurethane systems. These are commonly referred to as chain extenders.

Representative references which illustrate some of the early processes in forming ring alkylated aromatic amines are:

British Patent 414,574 discloses the reaction of aniline with various olefins, e.g., cyclohexene and alcohols, e.g., butanol in the presence of a neutral or weakly acidic catalyst system commonly referred to as hydrosilicates at temperatures from 200°–270° C. Ortho and para-cyclohexylaniline, N-cyclohexylaniline, N-butylaniline and para-methyl-ortho-cyclohexylaniline and N-cyclohexyl-para-toluidine are listed as representative products.

British Patent 846,226 discloses ring alkylation of aromatic amines with olefins using active, substantially neutral bleaching earths of the montmorillonite type as a catalyst.

AS 1,051,271 discloses the ring alkylation of aniline with an olefin, e.g., ethylene, in the presence of kaolin or in the presence of aluminum and aluminum alloys. Alkylation with higher olefins, e.g., propylene, butylene, etc., was carried out in the presence of Friedel-Crafts catalysts or bleaching earths under liquid phase conditions at temperatures from 150°–350° C. Examples of catalytic systems included aluminum chloride, zinc chloride, boron trifluoride, sulfuric acid, phosphoric acid and bleaching earth. Ring alkylation at the ortho-position was predominant, although other products such as the di and tri-alkylated aniline product were produced.

In an article by Zollner and Marton, Acta Chim. Hung. Tomus 20, 1959 (Pages 321–329) the vapor phase alkylation of aniline with ethanol was effected in the presence of aluminum oxide.

U.S. Pat. No. 3,649,693 and U.S. Pat. No. 3,923,892 discloses the preparation of ring alkylated aromatic amines by reacting an aromatic amine with an olefin in the presence of aluminum anilide, optionally including a Friedel-Crafts promoter. Reaction products included 2-ethylaniline, and 2,6-diethylaniline.

Stroh, et al., in U.S. Pat. No. 3,275,690; 2,762,845, Japanese Sho 56-110652, and, as mentioned previously, AS 1,051,271, disclose various processes for preparing alkylated aromatic amines by reacting an aromatic amine with an olefin in the presence of Friedel-Crafts catalysts as well as a combination of the Friedel-Crafts catalysts in the presence of halogen compounds combined with aluminum. Representative reaction products included 2-cyclohexylaniline, diethyltoluenediamine, diethylaniline, diisopropylaniline and mono-tert-butylaniline.

The art, e.g., Netherlands Application 6,407,636 has recognized that alkylation of various aromatic and heterocyclic compounds can be carried out in the presence of a zeolite having a pore size from 6–15 Angstroms wherein active cationic sites are obtained with an exchangeable metal or hydrogen cations in their ordered internal structure. Alkylating agents include olefins having from 2 to 12 carbon atoms, alkyl halides such as propylbromide and ethylchloride; and alkanols, such as, methanol, ethanol, and propanol. Various compounds were suggested as being suited for alkylation and these include both the heterocyclic and aromatic ring compounds. For aromatic amine alkylation it was suggested that a zeolite with a disperse distribution of acidic sites should be utilized. It was believed the highly acidic zeolite catalysts which have a high density of acidic sites may bind the amine to the catalyst and block the pore structures. In Example 1 aniline was alkylated with propylene using sodium zeolite X having a pore size of 13 Angstroms and numerous alkylated amines were produced. Example 3 shows alkylation of diphenylamine with cyclohexene using a rare earth exchanged 13 X zeolite. Again, numerous ring alkylated products were produced and high temperatures, e.g. 300° C. and above apparently being required to weaken the amine-acid bond.

French Patent 1,406,739, which is equivalent to Netherlands Application 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13X which has undergone a partial exchange with rare earths and having a pore size of 13A°.

Although the prior art has disclosed that a variety of catalytic systems can be utilized in the alkylation of aromatic hydrocarbons and aromatic amines, the art also teaches that a variety of reaction products are produced, including both ortho and para-isomers of mononuclear aromatic amines as well as, mono, di and tri alkyl substituted amines. In addition the prior art teaches that neutral to weakly acidic catalysts are preferred for effecting ring alkylation of the aromatic amines. Even though the prior art has suggested preferred catalytic systems such systems also involve batch, liquid phase operation which may be difficult to operate over an extended period of time, and tend to give more para product. In addition, many of the processes suffer from poor conversion, poor reaction rate, an inability to produce high ortho to para isomer ratios at high conversion and an inability to produce unsymmetrical amines.

SUMMARY OF THE INVENTION

This invention pertains to a process for effecting alkylation of aromatic amines typically represented by the formulas:

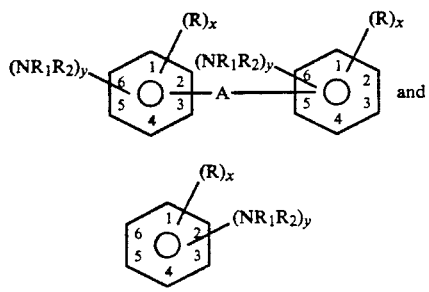

where R is hydrogen, $C_{1-10}$ alkyl or halogen; $R_1$ is hydrogen or $C_{1-10}$ alkyl, x is 1 or 2; A is $C_{0-4}$ alkylene or NH, y is 1 or 2 except one y in formula I can be zero.

Some of the advantages associated with this invention include:

an ability to selectively produce alkylated aromatic amines where the alkyl groups is in the ortho position, i.e., ortho relative to the amine group, as opposed to the para position, and the alkylation is effected at high conversion;

an ability to effect ring alkylation at high rates;

an ability to utilize a fixed bed catalytic reactor lending itself to continuous vapor or liquid phase operation;

an ability to form ortho-alkylates in high selectivity;

an ability to produce dialkylated aromatic amines having dissimilar alkyl groups and ortho to the amino group.

DETAILED DESCRIPTION OF THE INVENTION

As stated above ring alkylation of aromatic amines of this invention are represented by the formulas:

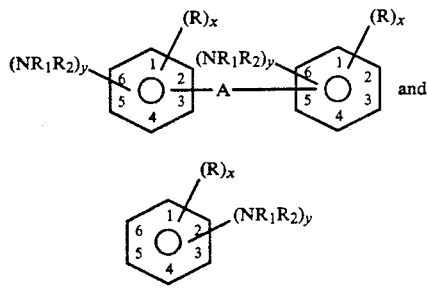

where R is hydrogen, $C_{1-10}$ alkyl or halogen; $R_1$ is hydrogen or $C_{1-10}$ alkyl; x is 1 or 2, A is $C_{0-4}$ alkylene or NH, y is 1 or 2 except one y in formula I can be zero.

As shown in the above formulas, the aromatic amine can be monoamino or diamino substituted on the aromatic ring. Further, the aromatic amine can be substituted with a variety of substituents which are nonreactive with the olefin in the alkylation reaction. Examples of nonreactive substituents include alkylamino where the alkyl portion has from 1-6 carbon atoms, such as N-ethyl, N-propyl and N-tert-butyl, alkyl where the alkyl substituent has from 1-6 carbon atoms, e.g. ethyl, propyl, tert-butyl and cyclohexyl, or methylcyclohexyl. Specific examples of aromatic amines suited for alkylation, which include those with active hydrogens in positions ortho and para to the amino group, are aniline, toluidine, xylidine, toluenediamine, xylidinediamine, methylenedianiline, ortho-ethyl aniline, ortho-propyl aniline, (N-propylamino)aminotoluene, ortho-isobutylaniline, phenyl aniline, phenylenediamine and methylbenzylaniline. Halogenated anilines, e.g., fluoroaniline can also be alkylated. Those aromatics amines suited for alkylation having active hydrogen atoms in positions ortho and para to an amino group include aniline and substituted derivatives, e.g., ethyl and propyl aniline where the alkyl group is ortho to the amine.

Alkylating agents used for practicing the invention are aliphatic, and cyclic olefins such as ethylene, propylene, butene isobutylene, isoamylene, cyclohexene, 1-methylcyclohexene, and 1-methylcyclopentene. Typically, these olefins will have from 2 to 8 carbon atoms in the structure.

In the alkylation of aromatic amines, the molar ratio of olefin to aromatic amine influences the selectivity of the reaction. In those cases where the aromatic amine can be alkylated in the ortho and para positions, the molar ratio of olefin to aromatic amine influences, to some degree, whether the ring alkylation is ortho to the amine or para to the amine. Typically olefin to amine molar ratios will range from about 1 to 20 moles olefin per mole of aromatic amine and preferably 2–8 moles olefin per mole of aromatic amine. The utilization of higher mole ratios of olefin to aromatic amine tends to increase the amount of ortho-alkylated product produced.

The catalyst used in the reaction of the present invention is gamma alumina a solid phase. Other aluminas; e.g., eta alumina, are not as active nor do they have the capability to effect alkylation of the amine to produce dissimilar dialkyl substituted aromatic amines.

The alkylation of aromatic amines to effect ring alkylation of the aromatic amine can be carried out in a fixed bed reactor with the reactants being fed downflow or upflow through the reactor. The reaction can also be carried out in a stirred autoclave. Temperatures from 50° to 425° C. and pressures of from 50 to 3000 psig are utilized. Although conversion of an aromatic amine to a ring alkylated product may be greater at temperatures near the upper end of the range specified, the degree of alkylation in the ortho-position e.g., alkylation as opposed to mono alkylation may be greatly increased and olefin polymerization may occur. Gamma alumina is unique because even at high temperatures it does not effect trialkylation or substantial para-alkylation as for example in the case of aniline.

Pressure has some effect on the selectivity to ortho-alkylated product but its effect is much less significant than temperature. Typically pressures used in the operation will range from 500 to 3000 psig for ethylene while pressures of from 50 to 1500 psig will be used for isobutylene.

Reaction time is an important factor in achieving high conversion. Broadly, the reaction time can be expressed as liquid hourly space velocity (LHSV) of feed components to the reactor and typical values for liquid hourly space velocity are from 0.05 to 6 hours$^{-1}$. If one is operating at relatively high temperatures for the alkylation reaction, the LHSV should be increased somewhat as longer reaction times may not be necessary to permit increased conversion.

Liquid phase or vapor phase conditions may be utilized in the practice of the invention and the process may be carried out on a batch or continuous basis. When a batch process is utilized the proportion of aromatic amine is from about 5 to 100 weight parts per weight part catalyst.

The following examples are provided to illustrate various embodiments of the invention and are not intended to restrict the scope thereof.

EXAMPLE 1

Alkylation of N-Isopropyl Aniline

A series of alkylation reactions was carried out in a fixed bed catalytic reactor, the reactor consisting of a 0.5" ID. 304 stainless steel tube which was jacketed with a single-element heater. A 5cc Vicor preheating bed was used to vaporize the reactants as they were passed downflow through the stainless steel tube jacketed reactor. The reactor was of sufficient length to accommodate from about 12-25 cubic centimeters of a solid phase catalyst system, having a particle size of from about 12-18 mesh (U.S. standard size). The reactions were conducted at temperatures at temperatures ranging from about 100°-400° C. and pressures of from about 50—1000 psig and an LHSV based upon total aromatic amine liquid feed to the vaporizer of from 0.05 to 4.0 hr.$^{-1}$.

The reaction product was collected and byproduct olefin was removed via vaporization. The reaction product then was analyzed (free of olefin) by gas chromatography using an internal standard technique.

Temperatures, pressures, catalysts, moles, olefin and amine reactant, and other variables are recited in Tables 1. Table 2 provides analytical results with respect to the run conditions described in Table 1. The run is an arbitrary run number to permit rapid identification of that data set in other Tables; temperature is in C°; pressure is in psig; G-Al$_2$O$_3$ refers to gamma-alumina, H-Y is a hydrogen exchanged Y zeolite, 13% Al$_2$O$_3$/SiO$_2$ refers to a silica-alumina catalyst containing 13% by weight of Al$_2$O$_3$. N refers to aromatic amine, i.e., aniline, R refers to olefin, e.g., propylene, X refers to N-alkylate, e.g., N-isopropylaniline, conversion (conv.) is expressed as percent and is based upon the total moles ring alkylated product produced divided by the total moles of aromatic amine and N-alkylated amine feed times 100; and o-p, refers to the ortho-para ratio which is the moles of 2+2,6-isomers divided by the moles of 4-isomer+2,4-isomer+2,4,6-isomer. In some cases an ortho to para ratio of >40 may have been written in, otherwise one would be dividing by zero.

Tables 1 illustrates the effect of various process parameters such as including catalyst activity on conversion. Other variables such as the mole ratio of olefin to total aromatic amine as well as the molar ratios of aniline to N-alkylate are shown. They are to be used in combination to observe trends; e.g., O-P ratios vs. conversion based upon reaction parameters. No one specific value is to be considered as controlling but rather is to be considered in combination with another value. The table product legends are as follows:

1. Aniline-aniline
2. N-IPA-N-isopropylaniline
3. 2-IPA-ortho-isopropylaniline
4. 4-IPA-para-isopropylaniline
5. N-2-DIPA-N,2-diisopropylaniline
6. 2,4-DIPA-2,4-diisopropylaniline
7. 2,6-DIPA-2,6-diisopropylaniline
8. 2,4,6-TIPA-2,4,6-triisopropylaniline

TABLE 1

CONVERSION OF N-ISOPROPYLANILINE
ARRANGED IN ASCENDING CONVERSION BY CATALYST TYPE

| RUN | TEMPERATURE | PRESSURE | N | R | X | CATALYST TYPE | Molar Feed Ratio LHSV | CONV | O-P |
|---|---|---|---|---|---|---|---|---|---|
| 5 | 348 | 900 | 0.50 | 0.00 | 0.50 | G-AL2O3 | 0.13 | 6.97 | >40 |
| 8 | 348 | 925 | 0.50 | 2.00 | 0.50 | G-AL2O3 | 0.13 | 32.98 | 31.82 |
| 11 | 348 | 860 | 0.00 | 10.00 | 1.00 | G-AL2O3 | 0.13 | 76.80 | 13.74 |
| 12 | 348 | 990 | 0.00 | 10.00 | 1.00 | G-AL2O3 | 0.13 | 77.63 | 14.35 |
| 13 | 348 | 990 | 0.00 | 10.00 | 1.00 | G-AL2O3 | 0.13 | 78.01 | 15.82 |
| 15 | 348 | 980 | 0.40 | 10.00 | 0.60 | G-AL2O3 | 0.13 | 80.42 | 19.35 |
| 14 | 348 | 990 | 0.40 | 10.00 | 0.60 | G-AL2O3 | 0.13 | 81.81 | 15.39 |
| 17 | 348 | 1000 | 0.40 | 10.00 | 0.60 | G-AL2O3 | 0.13 | 83.85 | 14.57 |
| 16 | 348 | 1000 | 0.40 | 10.00 | 0.60 | G-AL2O3 | 0.13 | 84.02 | 14.47 |
| 38 | 248 | 1073 | 0.00 | 2.00 | 1.00 | H-Y | 1.50 | 4.48 | >40 |
| 52 | 249 | 1003 | 0.75 | 2.00 | 0.25 | H-Y | 0.75 | 22.19 | 8.88 |
| 45 | 248 | 1035 | 0.50 | 2.00 | 0.50 | H-Y | 0.25 | 25.98 | 8.84 |
| 44 | 248 | 1033 | 0.50 | 2.00 | 0.50 | H-Y | 0.25 | 27.49 | 7.53 |
| 50 | 249 | 1060 | 0.00 | 2.00 | 1.00 | H-Y | 0.75 | 31.75 | 12.27 |
| 51 | 249 | 1054 | 0.00 | 2.00 | 1.00 | H-Y | 0.75 | 32.77 | 12.34 |
| 46 | 248 | 1013 | 0.75 | 2.00 | 0.25 | H-Y | 0.25 | 34.81 | 7.31 |
| 47 | 248 | 1026 | 0.75 | 2.00 | 0.25 | H-Y | 0.25 | 55.48 | 7.41 |
| 62 | 288 | 30 | 0.50 | 0.00 | 0.50 | 13% AL2O3/SIO2 | 0.18 | 15.53 | 2.63 |
| 67 | 290 | 930 | 0.75 | 2.00 | 0.25 | 13% AL2O3/SIO2 | 2.20 | 16.97 | 13.39 |
| 54 | 287 | 30 | 0.50 | 0.00 | 0.50 | 13% AL2O3/SIO2 | 0.18 | 17.16 | 2.63 |
| 68 | 290 | 930 | 0.75 | 2.00 | 0.25 | 13% AL2O3/SIO2 | 2.20 | 18.73 | 9.12 |
| 53 | 287 | 30 | 0.00 | 0.00 | 1.00 | 13% AL2O3/SIO2 | 0.18 | 25.08 | 2.34 |
| 63 | 288 | 890 | 0.50 | 2.00 | 0.50 | 13% AL2O3/SIO2 | 1.17 | 26.69 | 9.26 |

TABLE 2

| | CONVERSION OF N-ISOPROPYLANILINE | | | | | | | | | |
|---|---|---|---|---|---|---|---|---|---|---|
| RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
| 5 | 56.66 | 36.36 | 3.78 | 0.00 | 0.00 | 0.00 | 0.00 | 0.00 | 6.97 | >40 |
| 8 | 47.84 | 19.18 | 23.67 | 0.00 | 2.36 | 0.98 | 5.23 | 0.00 | 32.98 | 31.82 |
| 11 | 17.81 | 5.39 | 43.65 | 1.20 | 4.08 | 2.16 | 19.66 | 1.54 | 76.80 | 13.74 |
| 12 | 16.97 | 5.39 | 48.76 | 1.17 | 4.68 | 2.20 | 18.99 | 1.68 | 77.63 | 14.35 |
| 13 | 16.68 | 5.31 | 48.24 | 1.07 | 4.88 | 2.15 | 18.78 | 1.32 | 78.01 | 15.82 |
| 15 | 14.89 | 4.69 | 51.33 | 1.16 | 5.15 | 1.27 | 20.54 | 1.56 | 80.42 | 19.35 |
| 14 | 13.79 | 4.40 | 50.27 | 1.20 | 5.08 | 2.18 | 21.78 | 1.63 | 81.81 | 15.39 |
| 17 | 12.25 | 3.90 | 50.03 | 1.28 | 5.16 | 2.31 | 23.94 | 1.84 | 83.85 | 14.57 |
| 16 | 12.11 | 3.88 | 49.54 | 1.30 | 5.11 | 2.29 | 24.18 | 1.87 | 84.02 | 14.47 |
| 38 | 40.17 | 55.34 | 1.80 | 0.00 | 1.53 | 0.00 | 0.00 | 0.00 | 4.48 | >40 |
| 52 | 62.87 | 14.94 | 14.48 | 1.51 | 2.16 | 0.62 | 2.33 | 0.00 | 22.19 | 8.88 |
| 45 | 51.09 | 22.93 | 14.94 | 1.64 | 3.79 | 0.91 | 3.84 | 0.00 | 25.98 | 8.84 |
| 44 | 50.34 | 22.18 | 18.56 | 2.41 | 3.66 | 0.85 | 2.33 | 0.00 | 27.49 | 7.53 |
| 50 | 31.37 | 36.88 | 16.46 | 1.44 | 8.87 | 0.97 | 4.22 | 0.00 | 31.75 | 12.27 |
| 51 | 30.32 | 36.91 | 16.18 | 1.46 | 10.00 | 1.03 | 4.49 | 0.00 | 32.77 | 12.34 |
| 46 | 49.36 | 15.83 | 19.23 | 1.99 | 3.78 | 1.67 | 6.88 | 0.42 | 34.81 | 7.31 |
| 47 | 25.90 | 18.62 | 28.29 | 2.62 | 7.13 | 3.21 | 13.11 | 0.73 | 55.48 | 7.41 |
| 62 | 76.44 | 8.03 | 11.61 | 3.30 | 0.63 | 1.72 | 0.97 | 0.00 | 15.53 | 2.63 |
| 67 | 63.67 | 19.35 | 11.48 | 1.16 | 3.04 | 0.00 | 1.00 | 0.00 | 16.97 | 13.39 |
| 54 | 76.09 | 6.75 | 12.67 | 3.51 | 0.61 | 1.96 | 1.12 | 0.00 | 17.16 | 2.63 |
| 68 | 61.67 | 19.61 | 12.21 | 1.23 | 3.29 | 0.60 | 1.18 | 0.00 | 18.73 | 9.12 |
| 53 | 60.45 | 14.47 | 14.47 | 3.86 | 2.00 | 3.39 | 2.15 | 0.71 | 25.08 | 2.34 |
| 63 | 42.05 | 31.26 | 11.34 | 1.22 | 6.76 | 0.93 | 1.80 | 0.00 | 26.69 | 9.26 |

The results show that gamma-alumina was effective in producing high O-P ratios at high conversion. Although H-Y and silica-alumina can be driven to higher conversion, the O-P ratios drop.

EXAMPLE 2

The procedure of Example 1 was repeated, except that aniline was substituted for N-isopropylaniline. The LHSV based on aniline was 0.250 hrs.$^{-1}$ and the reaction was carried out at a pressure of 850 psig with a mole ratio of amine to olefin of 1:10. At a reaction temperature of 350° C. gamma-alumina resulted in conversion to ortho-isopropyline of 42.8% with a yield to 4-isopropylaniline of 0.08% while a catalyst of 13% alumina-87% silica at a reaction temperature of 252° C. resulted in the yield of 46.7% product based on aniline, with a yield of 0.86% of 4-isopropylaniline derivative. The silica-alumina catalyst also resulted in the production of diisopropylaniline with some in the form of 2,4-diisopropylaniline. A catalyst consisting of 18% phosphoric acid on silica at a temperature of 352° C. resulted in a 41.2% conversion of aniline to product with a yield of 4.8% 4-isopropylaniline.

This example shows the significant reduction of the para-substituted alkyl derivative of aniline by using gamma-alumina as compared to either silica-alumina or other acidic catalyst.

EXAMPLE 3

The procedure of Example 2 was repeated except that a fixed bed catalytic reactor was used and the reaction driven to higher conversions. An LHSV of 0.125 hrs. hours$^{-1}$, a pressure of 880 psig temperature of 352° C. and an amine to olefin ratio of 1:10 was used for a run employing gamma-alumina catalyst. Conversion of aniline to diisopropylaniline was 81% with 1.4% to the 2,4-diisopropylaniline isomer. When the reaction was repeated using a 13% alumina/87% silica catalyst at a temperature of 352° C., a space velocity of twice that used with gamma-alumina i.e., 0.25 hrs.$^{-1}$ a conversion of 99% was achieved, but with 13.8% being the 2,4-isopropylaniline isomer. Under similar conditions except a higher pressure (988 psig), but lower temperature (253° C.) an H-Y zeolite resulted in 92% conversion with 6% to the 2,4-diisopropylaniline derivative.

This example shows the enhanced selectivity with gamma-alumina in producing dialkyl substituted aniline derivatives, where the alkyl substituent is ortho to the amine groups with essentially no trialkyl substitution being achieved, or stated alternatively, no substitution at the 4 position. Trialkylation occurs with extended reaction times using silica-alumina catalyst, whereas substantially none is produced with gamma-alumina.

EXAMPLE 4

Process for Producing Ethylaniline

The procedure of Example 1 was repeated except that aniline was substituted for N-isopropylaniline and ethylene was substituted for the propylene. The catalyst utilized was gamma-alumina at a temperature of 375° C., a pressure of 727 psig, an amine ratio of aniline to ethylene of 1:10. The LHSV of the reaction based on aniline was 0.25 hrs.$^{-1}$. A conversion of approximately 24.8% was achieved with the reaction product containing 13% N-ethylaniline, 11% ortho-ethylaniline and 0.8% para-ethylaniline.

EXAMPLE 5

Aniline With Isopropanol

Example 4 was repeated except that isopropanol was substituted for ethylene. The reaction temperature was 302° C., the pressure was 850 psig, and a mole ratio of amine to alcohol was 1:10. Conversion was 32.2% with 27% of the aniline being converted to N-isopropylaniline. There was essentially no ortho-isopropylaniline derivatives or complex compositions. This example shows the ineffectiveness of gamma-alumina to catalyze the alkylation with an alkanol.

EXAMPLE 6

Preparation of 2-methyl-isopropylaniline

The procedure of Example 3 was repeated using the fixed bed catalytic reactor, except that ortho toluidine or rather 2-methyl-aniline was alkylated with propylene in the presence of gamma-alumina. Table 3 below sets forth the reaction conditions and product selectivity.

TABLE 3

Preparation of 2-methyl-isopropylaniline

| Run No. | Temp °C. | Pressure psig | LSHV* hr$^{-1}$ | N/R** | Conv. | % Product Selectivity*** | | | | 2,6/2,4 Isomer Ratio |
|---|---|---|---|---|---|---|---|---|---|---|
| | | | | | | N-iPr | 2-iPr | 4-iPr | (iPr)2-5 | |
| 1 | 322 | 850 | 0.125 | 1.0/5.0 | 19.59 | 37.72 | 58.55 | 2.25 | 1.48 | 26.0 |
| 2 | 352 | 930 | 0.125 | 1.0/5.0 | 39.04 | 13.19 | 78.46 | 2.23 | 6.15 | 35.2 |
| 3 | 352 | 930 | 0.06 | 1.0/5.0 | 59.00 | 6.37 | 83.81 | 1.41 | 8.40 | 59.4 |
| 4 | 352 | 920 | 0.03 | 1.0/5.0 | 65.70 | 4.73 | 83.04 | 1.34 | 10.87 | 62.0 |
| 5 | 375 | 900 | 0.125 | 1.0/3.0 | 44.40 | 6.78 | 76.87 | 3.13 | 13.22 | 24.6 |

*Based on 2-methylaniline flow rate only.
**Molar feed ratio of amine to olefin.
***Defined % selectivity = % molar yield/% conversion × 100%.

From the above results, it can be seen that only a small fraction of the isopropyl group is present in the 4 position, i.e., less than 5%; whereas the ortho-isopropyl derivative is present in concentrations of at least 55%. A further benefit of using gamma-alumina for this reaction is that the alkyl groups on the ring are dissimilar. Catalysts such as silica-alumina tend to effect transalkylation, and selectivity to compositions containing dissimilar alkyl groups is significantly lower.

EXAMPLE 7

Preparation of 2-fluoro-6-Isopropylaniline

The procedure of Example 6 was repeated, except that ortho-fluoroaniline was substituted for ortho-toluidine. An LHSV of 0.125 hr.$^{-1}$ and an N/R ratio of amine to olefin was 1:3. Table 4 sets forth the reaction conditions and results.

TABLE 4

Preparation of 2-fluoro-isopropylaniline

| Run No. | Temp °C. | Pressure psig | Conv. | % Product Selectivity*** | | | | 2,6/2,4 Isomer Ratio |
|---|---|---|---|---|---|---|---|---|
| | | | | N-iPr | 2-iPr | 4-iPr | (iPr)2-5 | |
| 1 | 325 | 900 | 54.99 | 18.24 | 43.92 | 11.66 | 26.19 | 3.8 |
| 2 | 350 | 900 | 56.09 | 9.20 | 44.29 | 15.01 | 31.50 | 3.0 |
| 3 | 350 | 900 | 45.94 | 1.69 | 44.58 | 17.76 | 25.97 | 2.5 |

*Based on 2-fluoroaniline flow rate only.
**Molar feed ratio of amine to olefin.
***Defined % selectivity = % molar yield/% conversion × 100%.
N-iPr refers to N-2-fluoro-N-isopropylaniline
2-iPr refers to 2-fluoro-6-isopropyl
4-iPr refers to 2-fluoro-4-isopropylaniline
iPr (2.5) refers to a mixture of 2-fluoro-diisopropylanilines From the results in Table 4, the amount of 4-isopropyl derivative increased as compared to the 4-isopropyl derivative of ortho-toluidine in Example 6. Nevertheless, the level of ortho-isopropyl derivative 2-fluoroaniline was substantial based upon the conversion and the 2,6-/2,4-isomer ratios were at least about 2-½ 4:1.

EXAMPLE 8

Preparation of 2-ethyl-6-isopropylaniline

The procedure of Example 6 was repeated, except that 2-ethylaniline was substituted for ortho-toluidine. Table 5 sets forth the reaction conditions and product selectivity.

TABLE 5

Preparation of 2-ethyl-6-isopropylaniline

| Run No. | Temp °C. | Pressure psig | LSHV* hr$^{-1}$ | N/R** | Conv. | % Product Selectivity*** | | | | 2,6/2,4 Isomer Ratio |
|---|---|---|---|---|---|---|---|---|---|---|
| | | | | | | N-iPr | 2-iPr | 4-iPr | (iPr)2-5 | |
| 1 | 325 | 900 | 0.125 | 1.0/3.0 | 16.60 | 44.76 | 45.60 | — | 9.70 | — |
| 2 | 350 | 900 | 0.125 | 1.0/3.0 | 32.38 | 15.81 | 69.58 | 0.93 | 13.71 | 75.1 |
| 3 | 375 | 900 | 0.125 | 1.0/3.0 | 54.60 | 3.99 | 74.19 | 2.11 | 19.72 | 35.2 |

*Based on 2-methylaniline flow rate only.
**Molar feed ratio of amine to olefin.
***Defined % selectivity = % molar yield/% conversion × 100%.

As can be seen from the data conversion was acceptable and essentially little to no para-isomer was produced.

What is claimed is:

1. In a process for alkylating aromatic amines by contacting said aromatic amine with an olefin in the presence of a catalyst system, the improvement for producing alkylated aniline and toluidine which comprises:

contacting aniline, toluidine or the N-alkylated derivatives thereof with an olefin selected from the group consisting of ethylene, propylene and isobutylene in the presence of a non-acid-activated gamma alumina wherein the reaction is carried out in a fixed bed catalytic rector and the liquid hourly space velocity is 0.05 to 6 hrs.$^{-1}$.

2. The process of claim 1 wherein the reaction temperature is from 50° to 425° C. and the aromatic amine is aniline or toluidine.

3. The process of claim 2 wherein the mole ratio of olefin to aniline or toluidine is from about 1-10:1.

4. In a process for alkylating ortho alkylaniline by contacting said aniline with an olefin in the presence of a catalyst system, the improvement for obtaining high conversion of alkyl-substituted anilines to alkylanilines having dissimilar alkyl groups, the improvement which comprises effecting said reaction of alkyl substituted alkylaniline with a $C_{2-6}$ olefin in the presence of gamma-alumina.

5. The process of claim 4 wherein the molar ratio of olefin to alkylaniline is from 1–10:1.

6. The process of claim 5 wherein said alkylaniline is ortho-methyl aniline and said olefin is ethylene, propylene, or isobutylene.

7. The process of claim 5 wherein said aniline is ortho-ethylaniline and said olefin is propylene.

8. The process for alkylating ortho-fluoroaniline with an olefin, the improvement for producing ortho-alkylated fluoroanilines which comprises contacting the fluoro-aniline with a $C_{2-6}$ olefin in the presence of gamma-alumina.

9. The process of claim 8 wherein said olefin is propylene or isobutylene.

* * * * *